(12) United States Patent
Borgschulte et al.

(10) Patent No.: US 8,720,432 B2
(45) Date of Patent: May 13, 2014

(54) INHALATION TREATMENT DEVICE AND METHOD FOR THE OPERATION THEREOF

(75) Inventors: Markus Borgschulte, Munich (DE); Wolfgang Achtzehner, Alling (DE)

(73) Assignee: PARI Pharma GmbH, Starnberg (DE)

( * ) Notice: Subject to any disclaimer, the term of this patent is extended or adjusted under 35 U.S.C. 154(b) by 1136 days.

(21) Appl. No.: 11/884,095

(22) PCT Filed: Jan. 16, 2006

(86) PCT No.: PCT/EP2006/000315
§ 371 (c)(1),
(2), (4) Date: Apr. 23, 2008

(87) PCT Pub. No.: WO2006/084543
PCT Pub. Date: Aug. 17, 2006

(65) Prior Publication Data
US 2009/0120431 A1 May 14, 2009

(30) Foreign Application Priority Data
Feb. 11, 2005 (DE) .................. 10 2005 006 372

(51) Int. Cl.
*A61M 11/00* (2006.01)
(52) U.S. Cl.
USPC .................................. 128/200.14
(58) Field of Classification Search
USPC .......... 222/23, 52, 63; 239/102.1, 102.2, 338, 239/370, 71
See application file for complete search history.

(56) References Cited

U.S. PATENT DOCUMENTS

| | | | |
|---|---|---|---|
| 5,551,416 A | 9/1996 | Stimpson et al. | |
| 5,735,263 A * | 4/1998 | Rubsamen et al. | 128/200.14 |
| 6,152,130 A * | 11/2000 | Abrams et al. | 128/204.21 |
| 7,009,517 B2 * | 3/2006 | Wood | 340/572.1 |
| 7,091,864 B2 * | 8/2006 | Veitch et al. | 340/572.8 |
| 7,191,780 B2 * | 3/2007 | Faram | 128/204.25 |
| 2002/0134377 A1 * | 9/2002 | Loeffler et al. | 128/200.24 |
| 2002/0157662 A1 * | 10/2002 | Stenzler | 128/200.16 |
| 2003/0183226 A1 * | 10/2003 | Brand et al. | 128/200.23 |
| 2005/0205089 A1 * | 9/2005 | Fink et al. | 128/203.15 |

FOREIGN PATENT DOCUMENTS

| | | |
|---|---|---|
| GB | 2 262 452 A | 6/1993 |
| WO | WO 02/17988 A2 | 3/2002 |
| WO | WO 2004/028606 A1 | 4/2004 |

OTHER PUBLICATIONS

International Preliminary Report on Patentability dated Aug. 23, 2007 from corresponding International Application No. PCT/EP2006/000315.

* cited by examiner

*Primary Examiner* — Rachel Young
(74) *Attorney, Agent, or Firm* — Wolf, Greenfield & Sacks, P.C.

(57) ABSTRACT

An inhalation nebulizer includes an aerosol generator that can be removed from the inhalation therapy device or inserted therein, and a control device that sends a control signal to the aerosol generator. The aerosol generator has a characterization device containing information about the aerosol generator, that can be determined by an identification device of the inhalation therapy device, in order to influence the operation of the inhalation therapy device.

25 Claims, 5 Drawing Sheets

4: liquid connection
6: electrical connection
8: signal connection
10: characterization device
11: identification device

Fig. 1

- 3: liquid reservoir
- 2: aerosol generator
- 5: control device
- 4: liquid connection
- 6: electrical connection
- 8: signal connection
- 10: characterization device
- 11: identification device

Fig. 2

10: characterization device

11: ID device

Fig. 3 aerosol generator — 2

10 (barcode)

6 identification device — 11

8

10: characterization device

10: characterization device 10-1: first terminals 11.1: second terminals

11: ID device

Fig. 5 aerosol generator 2

10a memory
10
10b 11b identification device 11

6

8

10b: connecting device

11b: connecting device

INHALATION TREATMENT DEVICE AND METHOD FOR THE OPERATION THEREOF

The invention relates to inhalation therapy devices with an aerosol generator that can be removed from the inhalation therapy device or inserted therein, as well as to a method for the operation thereof.

Aerosols for therapeutic purposes, which have to meet high requirements, are generated with inhalation therapy devices. The effort made to ensure quality during the design and manufacture of these devices is accordingly high. Various factors, however, have an effect on the functional capability and dose accuracy of the inhalation therapy device during use of the device by a patient.

Against this background, the object of the invention is to provide measures with which the functional capability and dose accuracy of an inhalation therapy device can be ensured.

The object is achieved according to the invention by a device having the features of claim 1 and a method according to claim 20. Advantageous designs can be seen in the subclaims.

The invention takes as a basis the idea that the key part of an inhalation therapy device of the type in question here is the aerosol generator, which is disposed in the inhalation therapy device and which generates an aerosol from a medicament present in the form of a liquid if it is controlled to generate an aerosol by a control unit present in the inhalation therapy device. The aerosol generator typically has at least one membrane and one oscillation generator, whereby the membrane can be caused to oscillate by the oscillation generator and then generates an aerosol from the liquid supplied to the one side of the membrane. Especially in high-quality inhalation therapy devices, the aerosol generator can be removed from the device in order, for example, to clean it thoroughly, to replace it with an aerosol generator of a different design or to check it for damage and replace it if faulty.

On the basis of this, the invention proposes to equip the aerosol generator with a characterisation device and the inhalation therapy device with an identification device which are connected with one another when the aerosol generator is inserted into the inhalation device so that the aerosol generator is checked immediately before and during operation by the inhalation device, and in this manner it is possible to ensure the functional capability and dose accuracy of the inhalation therapy device.

The characterization device creates the possibility of individualising the aerosol generator, i.e. providing it with information which characterises it and makes it distinguishable in relation to other aerosol generators of the same or a different design, and which in an advantageous design also offers the possibility of specifying varying properties/parameters of the aerosol generator. On the basis of this information, it can be determined in the inhalation therapy device, for example, whether an aerosol generator that is suitable for the inhalation therapy device has been used, whether the aerosol generator has already reached a preset maximum service life or whether properties/parameters determined during manufacture need to be taken into consideration during control.

Further possible applications and details of the invention can be seen from the following description of embodiments of the invention. Reference is thereby made to the drawings, in which:

FIG. 1 shows a block diagram with a schematic representation of the structure of an inhalation therapy device according to the invention;

FIG. 2 shows a block diagram with a schematic representation of a first embodiment of a characterization device and an identification device according to the invention;

FIG. 3 shows a block diagram with a schematic representation of a second embodiment of a characterization device and an identification device according to the invention;

FIG. 5 shows a block diagram with a schematic representation of a fourth embodiment of a characterization device and an identification device according to the invention.

Figure 4:
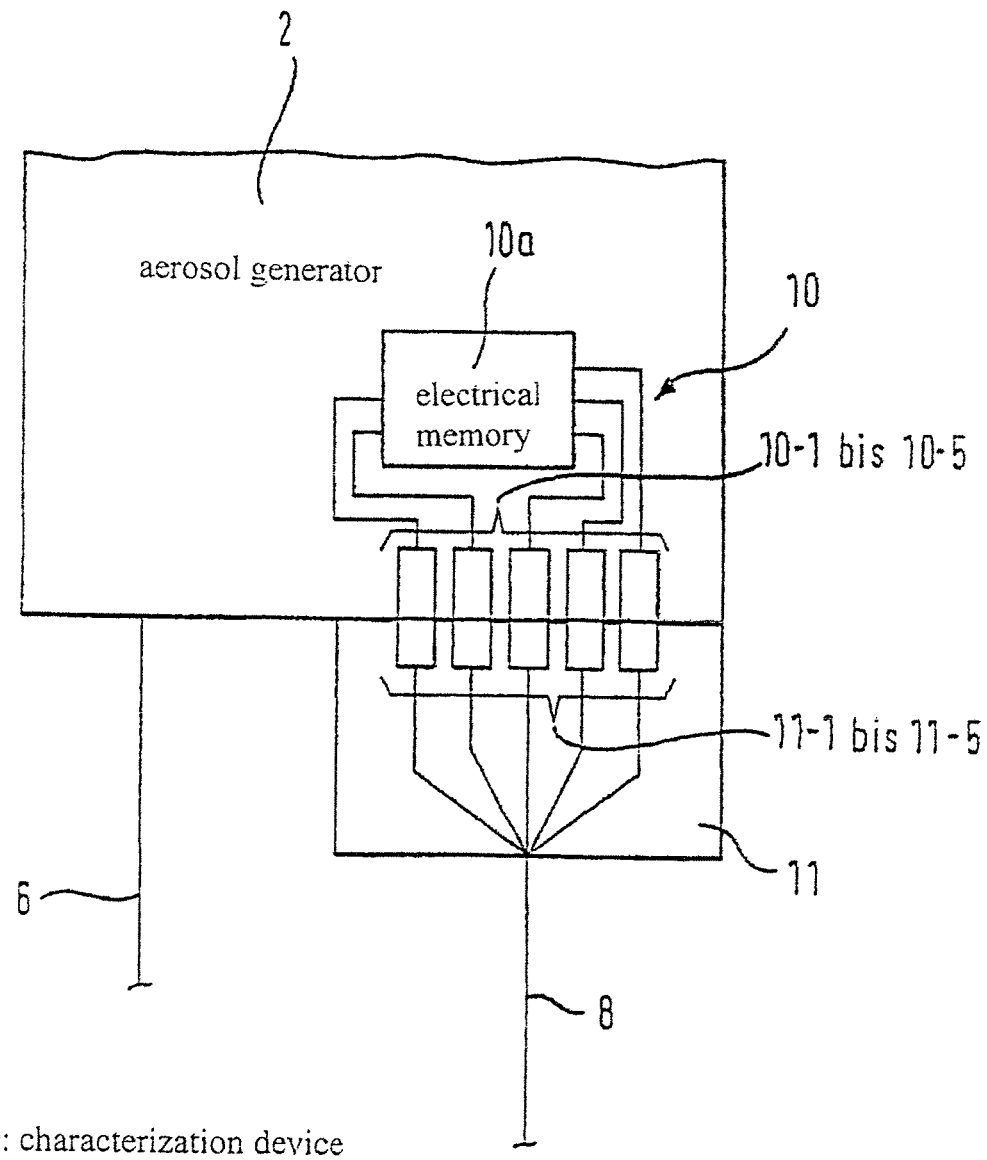
FIG. 4 shows a block diagram with a schematic representation of a third embodiment of a characterization device and an identification device according to the invention.

FIG. 1 shows, in a schematic representation, an inhalation therapy device 1 according to the invention, which comprises an aerosol generator 2 that is connected to a liquid reservoir 3 by way of a liquid connection 4 such that a liquid stored in the liquid reservoir 3 is supplied to the aerosol generator 2. A control device 5 supplies an actuating signal to the aerosol generator 2 via a mostly electrical connection 6, said signal causing the aerosol generator 2 to nebulize the liquid from the liquid reservoir 3 such that an aerosol 7 is generated. The aerosol 7 is offered to a patient for inhalation, for which purpose the inhalation therapy device 1 usually has a mouthpiece (not shown) or the like.

The aerosol generator 2 can be removed from the inhalation therapy device 1 or can be inserted into the same. For this reason, the liquid connection 4 and the control connection 6 are designed such that the respective connection is established when the aerosol generator 2 is inserted into the inhalation therapy device 1 and is separated when it is removed.

According to the invention, the aerosol generator 2 comprises a characterization device 10, in which at least such information I is stored that individualises the aerosol generator 2, i.e. which characterises it and makes it distinguishable in relation to other aerosol generators of the same or a different design. Practically as a counterpart, the inhalation therapy device 1 comprises an identification device 11, which cooperates with the characterization device 10, i.e. which can access at least the stored information in order to determine information I characterising the aerosol generator.

The information I regarding the aerosol generator 2 that is determined in this manner can be used in various ways. For example, the identification device 11 may be designed such that checking of the information or a comparison with reference information that is preferably stored in the identification device 11 or in a separate memory takes place and the control device 5 is activated or deactivated depending on the result. For this purpose, the identification device 11 supplies the control device 5 with an activation/deactivation signal by way of the signal connection 8 shown in FIG. 1. However, the identification device 11 preferably passes on information I to the control device 5 by way of an appropriately designed, preferably electrical, information connection 8.

There are various design possibilities as regards the characterization device 10 and the identification device 11.

Figure 2:
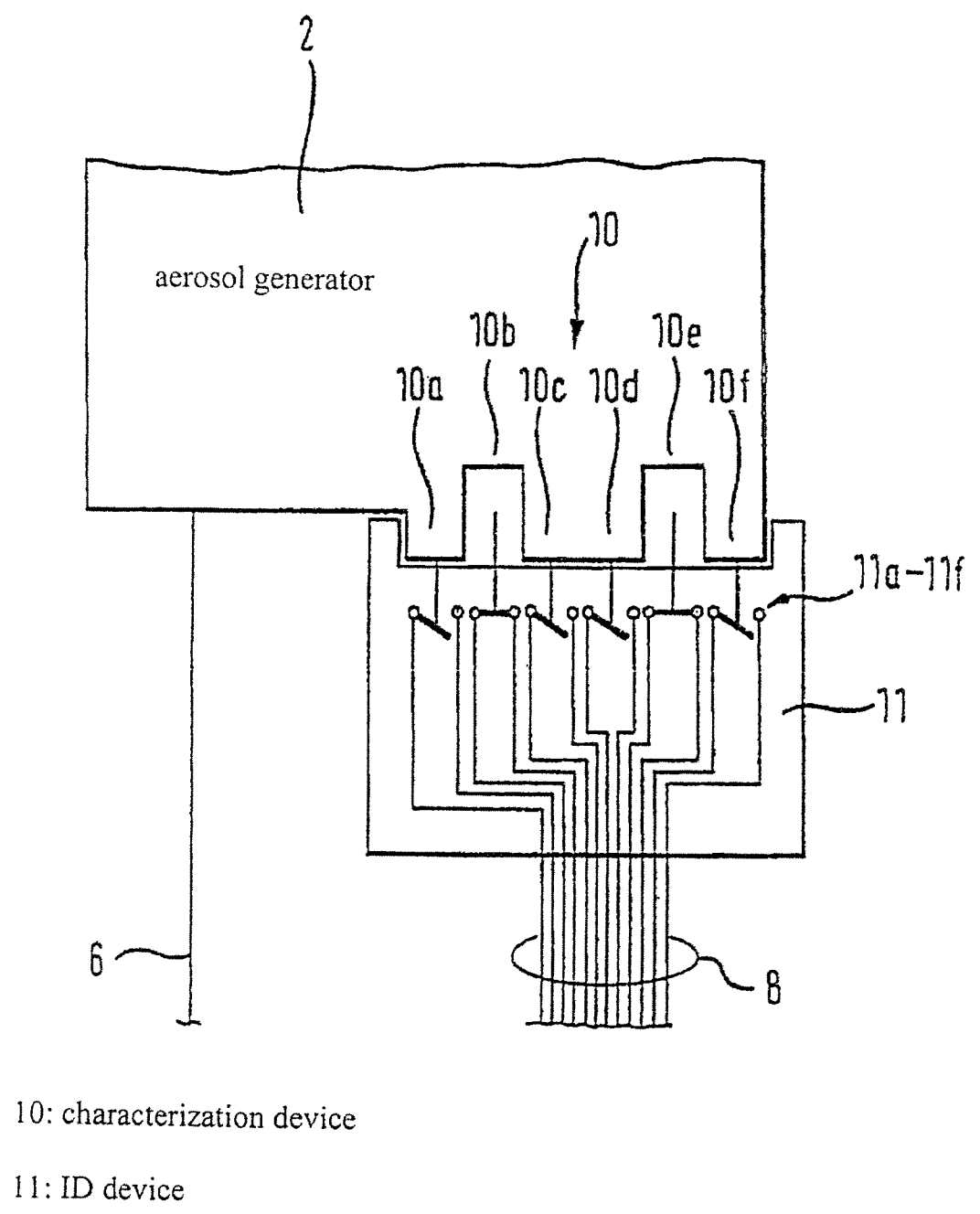

In a first design according to FIG. 2, in which only the section indicated in FIG. 1 is shown, the characterization device 10 is realized in the form of a plurality of recesses and/or projections 10a to 10f, which are provided on the outer surface of the aerosol generator 2 and the number and/or arrangement/sequence of which identifies the aerosol generator 2. The identification device 11 is realized, for example, as an arrangement of a corresponding number of switches 11a to 11f, as shown by way of example in FIG. 2, which are switched according to the arrangement of recesses and projections when the aerosol generator is inserted into the inhalation therapy device 1. Switches 11a to 11f are connected by way of the information connection 8 to the control device 5 such that information I can be used there.

In a second design according to FIG. 3, in which only the section indicated in FIG. 1 is shown, the characterization device 10 is realized in the form of a barcode sticker or barcode imprint on an outer surface of the aerosol generator 2. The identification device 11 is accordingly a barcode reader, which is disposed such that the content of the barcode sticker or barcode imprint can be read and the information stored in the barcode can be supplied by way of the information connection 8 to the control device 5 for use. Other machine-readable codes, e.g. dot matrix codes or 2D barcodes, may also be used instead of the barcode shown in FIG. 3.

In a third design according to FIG. 4, in which only the section indicated in FIG. 1 is shown, the characterization device 10 is realized in the form of an electrical memory 10a, which is connected to a plurality of first terminals 10-1 to 10-5 that are disposed on an outer surface of the aerosol generator 2. The identification device 11 has a corresponding number of second terminals 11-1 to 11-5, which contact the first terminals 10-1 to 10-5 when the aerosol generator 2 is inserted into the inhalation therapy device 1.

Any non-volatile memory, such as an EPROM for example, that is programmed during manufacture of the aerosol generator 2 and then stores the programmed contents without a power supply is suitable as the memory 10a. If, according to a preferred design, a non-volatile read/write memory is used, for example an EEPROM or a so-called flash memory, then it is possible to easily store not only during manufacture the desired information regarding the aerosol generator 2 in memory 10a but also to store information accrued during operation of the inhalation therapy device 1 in the memory of the aerosol generator 2. For this purpose, the control unit 2 is preferably equipped with a programming function.

According to a fourth design that is shown in FIG. 5, which only shows the section indicated in FIG. 1, the memory 10a is not connected to terminal contacts but to a contactless first connecting device 10b. The identification device 11 comprises a corresponding contactless second connecting device 11b which ensures a connection to the first connecting device 10b when the aerosol generator 2 is inserted into the inhalation therapy device 1. The content of the memory 10a is then read out by the identification device 11 via the connection established by means of the two contactless connecting devices 10b and 11b, and the thus determined information regarding the aerosol generator 2 is passed on by the identification device 11 to the control device 5. The contactless connection may be effected by means of radio or light, preferably infrared light, or by magnetic means.

The information regarding the aerosol generator 2 which is stored in the characterization device 10 can relate to the most diverse aspects of the aerosol generator 2 and may be included in various ways in the operation of the aerosol generator and/or the inhalation therapy device. The control device 5 generally assumes the task of including the determined information into the control of the aerosol generator 2 and—in as far as provided—of storing information in the characterization device which was not available at the time the aerosol generator 2 was manufactured and which has only arisen during operation of the inhalation therapy device 1.

The information stored in the characterization device 10 of an aerosol generator 2 according to the invention is, for example, the following information which can be stored during production:

type details, which include a type designation and/or operating parameters (e.g. control voltage, resonant frequency, etc.) of the aerosol generator;
manufacturing information such as the date of manufacture and/or a batch identifier;
a maximum period of use;
a maximum service life;
a maximum number/frequency of use;
permissible therapy applications.

Insofar as information can be stored in the characterization device 10 during operation of the inhalation therapy device 1, the following information may also be provided:
date of first use;
actual service life;
actual number/frequency of use.

In an inhalation therapy device 1 according to the invention, the control device 5 is advantageously realized in a program-controlled form such that inclusion of the information determined from the characterization device can be realized to a large extent without problems. The use of some of the information specified above for the control of the aerosol generator 2 will be described by way of example in the following and it can be recognized that this is associated in each case with safeguarding the operation of the inhalation therapy device according to the invention.

The control device 5 may be designed such that it is determined on the basis of the ascertained type designation whether the inserted aerosol generator 2 is suitable/permissible for use with the inhalation therapy device 1. In this way it is ensured that an unsuitable aerosol generator is not used in the inhalation therapy device.

By including determined operating parameters, it is possible, for example, to ensure that the control device 5 emits a control signal to the aerosol generator 2 which has the correct parameters, such as the correct voltage and the correct frequency. This prevents the inhalation therapy device from being used with an aerosol generator which is wrongly controlled in this respect but at the same time creates the possibility of being able to use different aerosol generators in the inhalation therapy device.

Based on the determined date of manufacture, the control device 5 can determine, with reference to a current date that is provided, for example, by a timer integrated in the control device, whether the aerosol generator 2 may still be operated or not. In a similar manner, the control device 5 is able to determine whether a maximum period of use, a maximum service life or a maximum number/frequency of use has yet been reached. This ensures that the aerosol generator will no longer be used if there is a risk that inadmissible nebulization results, which would negatively affect the dose accuracy of the inhalation therapy device, will be achieved due to the long periods or frequent use.

An inhalation therapy device according to the invention is characterized by a high level of flexibility despite the high degree of safe-guarding of functional capability and dose accuracy. This is because control of the aerosol generator 2 can be carried out in various ways, for example based on different control signals, depending on the type determined. For this purpose, the control device 2 has various control scheme which are assigned in each case to one or more types of aerosol generator such that control takes place according to the assigned scheme or to a scheme selected from the assigned scheme. The control schemes specify, for example, resonant frequencies, switch-on times/delays, switch-off times/delays and/or signal progressions, which can be used as the basis for generating the control signal. The control schemes/programs are preferably stored in a memory of the control device 5, which may be designed as a data/parameter memory, in which data is stored for generating the control signal, or as a program memory, in which various programs for generating the control signal are stored, said programs being selected and executed depending on the information characterizing the aerosol generator.

The operation of an inhalation therapy device 1 according to the invention is characterized by the step of determining information I characterizing the aerosol generator 2, i.e. in that the identification device 11 retrieves the information from the characterization device 10. In a particular design, the control device 5 is activated or deactivated on the basis of at least one part of the information, as was described above. In a specific design, it is checked whether use of the aerosol generator is permitted in the inhalation therapy device or whether a maximum usage of the aerosol generator has been reached. In a further design, a control scheme/program for generating the control signal is selected on the basis of at least one part of the information.

The invention claimed is:

1. Inhalation therapy device, comprising:
   a liquid reservoir for storing a liquid,
   a removable aerosol generator, which can be inserted into the inhalation therapy device or removed from the inhalation therapy device and to which a control signal can be supplied for aerosol generation,
   a liquid connection for supplying said liquid to said removable aerosol generator, and
   a control device for providing the control signal that is supplied to the removable aerosol generator inserted in the inhalation therapy device during aerosol generation,
   whereby said liquid connection is adapted to establish a connection when said removable aerosol generator is inserted into said inhalation therapy device,
   wherein
   the removable aerosol generator is provided with a characterization device such that the characterization device is removable from said liquid reservoir together with said removable aerosol generator, said characterization device being for the provision of information characterizing operating parameters of the removable aerosol generator and making it distinguishable in relation to other aerosol generators of the same or different design and/or specifications; and
   the inhalation therapy device comprises an identification device, which co-operates with the characterization device of the removable aerosol generator inserted in the inhalation therapy device for determining the information characterizing the removable aerosol generator.

2. Inhalation therapy device according to claim 1, wherein the identification device activates or deactivates the control device based on the determined information characterizing the removable aerosol generator, wherein the identification device supplies an activation or deactivation signal to the control device.

3. Inhalation therapy device according to claim 1, wherein the identification device supplies the determined information characterizing the removable aerosol generator to the control device.

4. Inhalation therapy device according to claim 1, wherein the characterization device comprises a plurality of recesses/projections on a surface of the removable aerosol generator and the identification device comprises an arrangement of a corresponding number of switches, the switch having switch positions of which are influenced by the recesses/projections when the removable aerosol generator is inserted in the inhalation therapy device.

5. Inhalation therapy device according to claim 1, wherein the characterization device comprises a barcode sticker or barcode imprint on a surface of the removable aerosol generator and the identification device comprises a barcode reader.

6. Inhalation therapy device according to claim 1, wherein the characterization device comprises an electrical memory.

7. Inhalation therapy device according to claim 6, wherein the memory is connected to a plurality of first terminals which are each in contact with a terminal of a plurality of second terminals when the removable aerosol generator is inserted into the inhalation therapy device.

8. Inhalation therapy device according to claim 6, wherein the memory is connected by means of a contactless first connecting device to a corresponding contactless second connecting device of the identification device.

9. Inhalation therapy device according to claim 6, wherein the memory is a non-volatile memory.

10. Inhalation therapy device according to claim 6, wherein the memory is a non-volatile read/write memory.

11. Inhalation therapy device according to claim 1, wherein the information characterizing the removable aerosol generator further includes one or more of the following details:
   type details, which include a type designation and/or control voltage and/or resonant frequency of the removable aerosol generator;
   manufacturing information, and/or date of manufacture and/or a batch identifier;
   a maximum period of use;
   a maximum service life;
   a maximum number/frequency of use;
   permissible therapy applications;
   date of first use;
   actual service life;
   actual number/frequency of use.

12. Inhalation therapy device according to claim 1, wherein the control device is designed to ascertain, on the basis of the information determined, whether the inserted removable aerosol generator is suitable/permissible for the inhalation therapy device.

13. Inhalation therapy device according to claim 1, wherein the control device is designed to ensure, on the basis of the information determined, that the control signal with correct parameters, such as voltage and frequency, is supplied to the removable aerosol generator.

14. Inhalation therapy device according to claim 1, wherein the control device is designed to ascertain, on the basis of the information determined, whether the removable aerosol generator may still be operated against the background of too long or too frequent a use.

15. Inhalation therapy device according to claim 1, wherein the control device is designed to ascertain, on the basis of the information determined, which of a number of control schemes/programs are to be used as the basis for generating the control signal for the removable aerosol generator.

16. Inhalation therapy device according to claim 15, wherein the control device has a memory for the control schemes/programs.

17. Inhalation therapy device according to claim 1, wherein the control device is designed to store information in the characterization device.

18. Inhalation therapy device according to claim 1, wherein the removable aerosol generator has a membrane and an oscillation generating device.

19. Inhalation therapy device according to claim 18, wherein the liquid stored in the liquid reservoir is supplied to one side of the membrane.

20. Method for the generation of an aerosol using an inhalation therapy device having the features of claim 1, comprising the step of determining the information characterizing the removable aerosol generator.

21. Method according to claim 20, comprising the step of examining at least a part of the information determined and the step of activating or deactivating the control device.

22. Method according to claim 20, comprising the step of examining at least a part of the information determined and the step of checking whether the use of the removable aerosol generator in the inhalation therapy device is permissible.

23. Method according to claim 20, comprising the step of examining at least a part of the information determined and the step of checking whether a maximum use of the removable aerosol generator has been reached.

24. Method according to claim 20, comprising the step of examining at least a part of the information determined and the step of selecting a control diagram/program.

25. Inhalation therapy device according to claim 6, wherein the operating parameters comprise a control voltage and/or resonant frequency of the removable aerosol generator.

* * * * *